United States Patent [19]

Dewanckele et al.

[11] Patent Number: 5,236,815
[45] Date of Patent: Aug. 17, 1993

[54] CLASS OF MASKED STABILIZERS IN PHOTOGRAPHIC MATERIALS OR DEVELOPING SOLUTIONS

[75] Inventors: Jean-Marie O. Dewanckele, Drongen; Richard A. Ooms, Hofstade; Marc B. Graindourze, Overpelt; Piet Kok, Gent, all of Belgium

[73] Assignee: Agfa-Gevaert, N.V., Mortsel, Belgium

[21] Appl. No.: 923,483

[22] Filed: Aug. 3, 1992

[30] Foreign Application Priority Data

Aug. 13, 1991 [EP] European Pat. Off. ......... 91202073.2

[51] Int. Cl.$^5$ ............................................. G03C 5/26
[52] U.S. Cl. .................................... 430/448; 430/486; 430/489; 430/490; 430/523; 430/551; 430/607; 430/613
[58] Field of Search ............... 430/448, 486, 489, 490, 430/523, 551, 607, 613

[56] References Cited

FOREIGN PATENT DOCUMENTS 1922628 11/1970 Fed. Rep. of Germany .

OTHER PUBLICATIONS

CA 75(26): 152988q. Dec. 27, 1991.

*Primary Examiner*—Hoa Van Le
*Attorney, Agent, or Firm*—Breiner & Breiner

[57] ABSTRACT

A new class of photographic masked stabilizers is disclosed showing following general chemical formula (Ia) or (Ib):

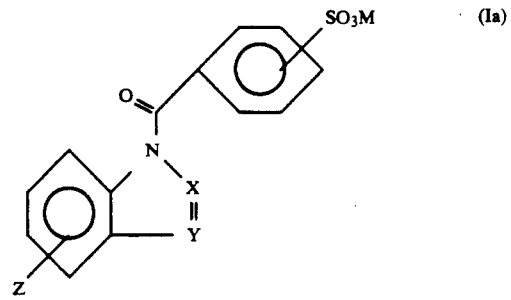

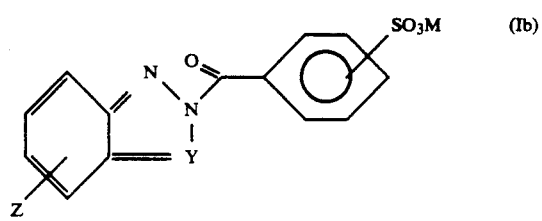

wherein
X and Y each independently represent N or CR, R being hydrogen or lower alkyl,
Z represents a lower alkyl group, a nitro group, a halogen atom or hydrogen, and
M represents a positive counterion, preferably an alkali cation, ammonium or substituted ammonium.

The compounds are demasked by hydrolysis under alkaline conditions. They can be incorporated in a developing solution or in a photographic material, preferably in the backing layer. They show an enhanced solvability in water compared to the corresponding unmasked stabilizers.

A preferred compound is 1-(2-sulphonatobenzoyl)-5-nitroindazole trimethylamine, sodium or potassium salt.

11 Claims, No Drawings

CLASS OF MASKED STABILIZERS IN PHOTOGRAPHIC MATERIALS OR DEVELOPING SOLUTIONS

DESCRIPTION

1. Field of the Invention

The present invention relates to photographic silver halide materials and to photographic developing solutions containing compounds representative for a new class of masked stabilizers.

2. Background of the Invention

In conventional silver halide photography so-called stabilizers or anti-foggants are well known ingredients which can be incorporated in photographic materials and/or in photographic developing solutions. Their principal function consists in minimizing the obtained fog level on developing exposed photographic materials and/or to reduce the rise of development fog after prolonged storage of the photographic material compared to the fog level of a freshly coated material. Numerous chemical classes of stabilizers are disclosed in photographic scientific and patent literature. Suitable examples are e.g. the heterocyclic nitrogen-containing compounds such as benzothiazolium salts, imidazoles, nitroimidazoles, benzimidazoles, nitrobenzimidazoles, chlorobenzimidazoles, bromobenzimidazoles, indazoles, nitroindazoles, mercaptothiazoles, mercaptobenzothiazoles, mercaptobenzimidazoles, mercaptothiadiazoles, aminotriazoles, benzotriazoles (preferably 5-methyl-benzotriazole), nitrobenzotriazoles, mercaptotetrazoles, in particular 1-phenyl-5-mercapto-tetrazole, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2-58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, toluenethiosulphonic acid, benzenethiosulphinic acid and benzenethiosulphonic acid amide. A review of useful compounds is published in Research Disclosure No. 17643 (1978), Chapter VI.

Preferred classes of stabilizers are indazoles, benzimidazoles and benzotriazoles and their derivatives. However several useful representatives of these chemical classes of stabilizers show the disadvantage of a low solubility in water. For example the solubility of 5-methylbenzotriazole is limited to 0.5 g/100 ml of water and the solubility of 5-nitroindazole amounts to only 0.02 g/100 ml of water. Due to this low solubility these compounds have to be predissolved in organic solvents before incorporation in a photographic material or developing solution. In the first case this can lead to colloidal instability of the coating solution especially when the concentration of the binder, e.g. gelatin, is rather low: in the latter case the presence of organic solvents is undesirable from an ecological point of view.

Indazoles, benzimidazoles and benzotriazoles, and in particular their nitro-derivatives are especially useful compounds when present in so-called "hard dot Rapid Access" developers or materials, belonging to the graphic arts pre-press sector.

In graphic arts reproduction processes the original image appearing to have a continuous tone gradation is reproduced by a collection of a large number of dots and/or lines. The tone of the reproduced image is influenced by both the size of the dots and lines and their density. A graphic arts film exposed in a way to exactly render the relative proportions of black and white in the original must produce dots and lines of sufficient density. Therefore a photographic element showing high contrast or so-called "lith gradation" on development is highly desired. Furthermore the generaled or reproduced dots and lines must exhibit a well-shaped form and sharp edges. This most desired combination of high contrast and excellent dot quality is commonly termed "lith quality". The goal of achieving optimal lith quality is reached by the combination of specially designed graphic arts materials and appropriate processing systems. A first group of such processing systems consists of the traditional "lith developers" which however are rather instable in time and require complicated replenishment systems for both oxidation and exhaustion. In more recent times so-called "hard dot Rapid Access" developers and appropriate materials were introduced on the market which combine a good stability with a "lith quality" in the reproduction of lines and screen dots. Examples of such developers and corresponding appropriate photographic materials include the GRANDEX system, marketed by FUJI PHOTO Ltd. AGFA-STAR, marketed by AGFA-GEVAERT N.V. and the ULTRATEC system. marketed by EASTMAN KODAK Co.

Materials of this type include rather sensitive camera materials for the conversion of continuous tone originals into screened images and insensitive duplicating materials, e.g. of the daylight type. In the first case the halide composition of the silver halide emulsion(s) will mainly consist of bromide while in the latter case chloride will be the predominant halide ion. Several publications disclose the presence of a nitroindazole or nitrobenzimidazole in this type of material or developing solution. So U.S. Pat. No. 3,972,719 discloses a developer composition containing a p-hydroxybenzene developing agent, a sulphite compound providing at least 5 g/l of sulphite ions, a nitro-indazole and a polyalkyleneoxide. U.S. Pat. No. 4,756,990 discloses a method for high contrast development comprising a similar developer composition further containing an auxiliary developing agent. U.S. Pat. No. 4,710,451 describes a similar method comprising a predominantly bromide containing emulsion and a similar developer composition. DE 2.360.638 discloses a developer containing a hydroquinone, an indazole, e.g. a nitroindazole, and an organic solvent. Finally Unexamined Japanese Patent Publication (Kokai) No. 59-79251 describes a developing composition comprising a hydroquinone, sufficient sulphite, a nitroindazole, a polyalkyleneoxide and an organic solvent.

In developing compositions of the type cited above the nitroindazole or derivative is considered as a regulator of development kinetics. As a consequence it is of uttermost importance that during continuous processing of large amounts of photographic materials the concentration of the nitroindazole or derivative should be kept constant between very narrow limits in order to assure a constant quality of the developed image. However during continuous processing the amount of nitroindazole in the developer is partially depleted e.g. due to salt formation with unreduced silver ions leached out of the photographic material. In the case of processing of materials containing emulsions rich in bromide the decrease of the nitroindazole concentration is counteracted by the increase in bromide ion concentration due to the development reaction. It was established experimentally that nitroindazole and bromide ions influence the reaction kinetics in opposite ways so that they can counterbalance each others effect. However in the case of processing of large amounts of photographic materials containing emulsions rich in chloride the rising amount of chloride in the developing solution is unable to counteract the decreasing amount of the nitroindazole derivative. In this way the development reaction mechanism is disturbed and it is no longer possible to obtain constant and satisfying sensitometric and screen dot quality results. An elegant solution to this problem would consist in incorporating a sufficient amount of nitroindazole in the photographic material itself, e.g. in a backing layer. In this way extra nitroindazole could be leached out of the material during continuous processing and compensate for the decreasing amount of the nitroindazole originally present in the developer. In most cases unfortunately the realisation of this solution is prohibited by the spare solubility of nitroindazoles. If one tries to incorporate more nitroindazole in a photographic coating composition by means of addition of an organic solvent crystallization problems are likely to occur in the coating composition during the period between preparation and coating, or the colloid binder can become unstable as was explained above.

From the foregoing it is clear that there is a permanent need for more water soluble stabilizers or, alternatively, for water soluble substituted stabilizers, so-called "masked stabilizers" or "stabilizer precursors" which are able to set free well-known and useful but sparely soluble stabilizers during development.

It is an object of the present invention to provide a new class of such masked stabilizers.

It is a further object of the present invention to provide a method of developing photographic materials in the presence of such stabilizer precursors.

It is a still further object of the present invention to provide developing solutions, or separate parts of developing solutions ("part B") to be mixed with the main part ("part A) just before use, containing a member of this new class of masked stabilizers.

It is still a further object of the present invention to provide photographic materials containing a representative of this new class of masked stabilizers.

A still further object of the present invention is to provide a method for keeping the concentration of a free stabilizer, e.g. nitroindazole, constant in a developing solution.

SUMMARY OF THE INVENTION

The objects of the present invention are realised by providing a new class of stabilizer precursors according to following general chemical formula (Ia) or (Ib):

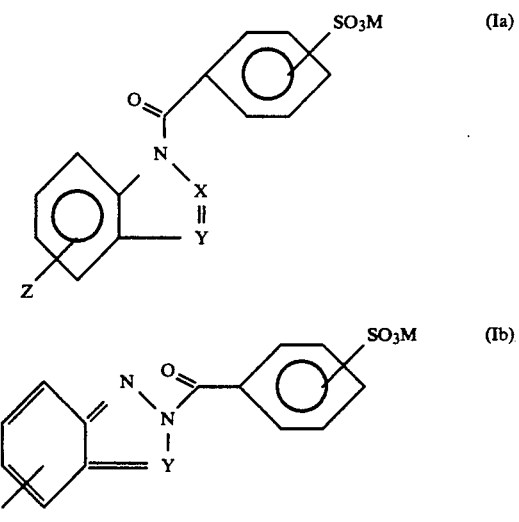

wherein X and Y each independently represent N or CR, R being hydrogen or lower alkyl, Z represents a lower alkyl group, a nitro group, a halogen atom or hydrogen, and M represents a positive counterion, preferably an alkali cation, ammonium or substituted ammonium.

The compounds of the invention show an enhanced solvability in water compared to the corresponding unmasked stabilizers. They can be incorporated as aqueous solutions in a developer or in a photographic material, e.g. in an emulsion layer or in a non-light sensitive layer, e.g. a backing layer. They are easily demasked, as was stated experimentally, by hydrolysis of the N—CO bond under alkaline conditions.

DETAILED DESCRIPTION OF THE INVENTION

Preferred examples of useful compounds according to the invention are given below:

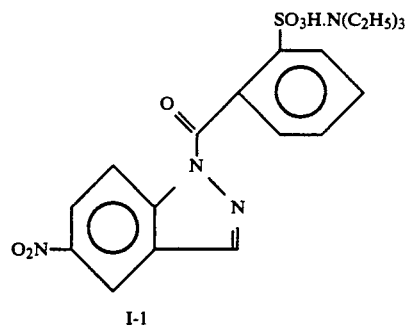

I-1

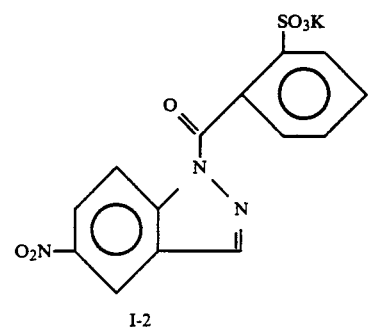

I-2

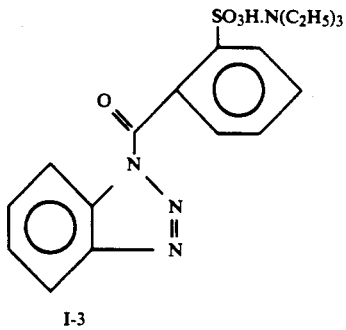

I-3

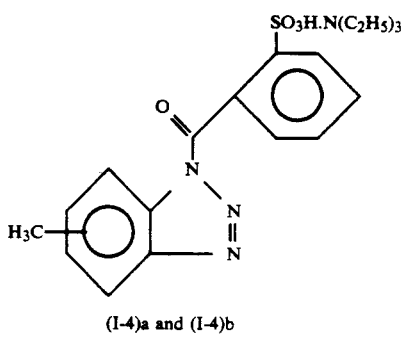

(I-4)a and (I-4)b

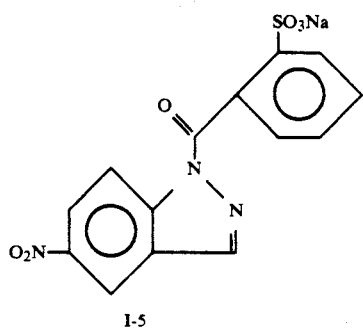

I-5

Note: formulae (I-4)a and (I-4)b represent two position isomers whereby the heterocyclic ring can be substituted by the methyl group on the 5-position or on the 6-position.

As can be seen from the list above all preferred examples belong to general formula Ia wherein the heterocyclic ring is substituted by the benzoyl part of the molecule at the 1-position. However during the acylation of indazole or benzotriazole derivatives in order to prepare the precursors of the invention a minor part (maximally 30% depending on the reaction conditions) of structural isomers with the benzoyl group at the 2-position can be formed (general formula Ib). These compounds form part of the invention too because on demasking they give rise to the same free stabilizers. For the same reason a mixture of a compound Ia and its corresponding compound Ib can be used successfully and forms part of the invention.

Some figures illustrate the improved water solubility of the stabilizer precursors compared to the free stabilizers: compound I-2 has a solubility at room temperature of 1.7 g/100 ml compared to only 0.02 g/100 ml for 5-nitroindazole; compound I-3 and I-4 show a solubility of 5.8 and 16.0 g/100 ml respectively against 1.3 for benzotriazole and 0.5 for 5-methylbenzotriazole.

Thanks to their sufficient solubility the compounds of the invention are incorporated in photographic coating compositions or developing solutions preferably simply in the form of aqueous solutions in a concentration dependent on their particular solubility, e.g. about 1% to about 10% solutions. In developers the compounds are preferably present in a concentration between 0.1 and 6 mmole/l and most preferably in a concentration between 0.4 and 0.8 mmole/l. In a coated photographic layer the compounds are preferably incorporated in a concentration ranging from 0.5 to 10.0 mmole/$m^2$ and most preferably in a concentration ranging from 1.0 to 5.0 mmole/$m^2$.

The application of the compounds of the invention is not limited to any particular kind of photographic material or its corresponding developing solution. So these compounds can be incorporated into black-and-white or colour materials for amateur or professional photography, black-and-white or colour materials for cinematographic recording or duplication, in radiographic recording or duplicating films, in graphic arts camera or duplicating materials, in films or papers suited for exposure to laser light, in holographic materials and in diffusion transfer reversal materials. In a preferred embodiment however these compounds are incorporated in the materials and/or developers of "hard dot Rapid Access" graphic arts systems. Developers of this kind usually contain stabilizers or development regulators, preferably 5-nitroindazole or a derivative, as disclosed in the references cited above. In preparing developers of this kind it is impossible to add 5-nitroindazole in the form of a concentrated aqueous solution because of its spare solubility and usually it is predissolved in an organic solvent, e.g. N-methyl-pyrrolidone. According to this invention a corresponding precursor like compound I-1 or I-2 is added in water. After hydrolysis in the alkaline finished developer the free 5-nitroindazol is diluted enough (range about 50 to 150 mg/l) to stay in solution.

In the particular application of compensating for the decreasing concentration of the unmasked stabilizer in the developer during continuous processing, explained above, the masked compound is added to the photographic material itself. In this case it can be added to any colloidal layer of the material, e.g. the emulsion layer, a backing layer, an intermediate layer or the protective layer. Preferably it is incorporated in the backing layer in order to avoid unwanted interactions with other emulsion layer ingredients. In this case too the stabilizer can be added as a simple aqueous solution to the coating composition avoiding the use of e.g. alcoholic solutions as would be the case with an unmasked compound like 5-nitroindazole.

The developing solutions to which the compounds of the invention can be added preferably contain one or more developing agents, sulphite ions, bromide ions and polyalkyleneoxides. Preferred developing agents are e.g. hydroquinone and derivatives, 3-pyrazolidinone derivatives like 1-phenyl-5-pyrazolidinone ("Phenidone") and analogues, aminophenols, hydroxylamin, hydrazine derivatives, ascorbic acid and analogues, and p-phenylene derivatives in the case of colour development. In the preferred embodiment of hard dot Rapid access materials a hydroquinone is substantially the only developing agent. Other adjuvants well known to those skilled in the art may be added to the developer liquid of the present invention. A survey of conventional developer addenda is given by Grant Haist in "Modern Photographic Processing"—John Wiley ans Sons—New York (1979) p. 220-224. Examples of such addenda include complexing agents for calcium and magnesium ions, present in hard water, e.g. ethylene diamine tetraacetic acid and analogues compounds. Further can be present anti-foaming agents, surface-active agents, biocides, thickening agents like polystyrene sulphonate and antioxidants like benzoate and cyclodextrine. The developing liquid can contain so-called anti-sludge agents in order to reduce dirt streaks on developed photographic material. The alkaline pH value of the developing solution is preferably established by means of conventional buffering agents like phosphate buffers, carbonate buffers and borax buffers. The pH can be additionally adjusted to the desired value by means of an alkali hydroxide, e.g. sodium or potassium hydroxide. Finally the solution can contain hardening agents including latent hardeners.

The photographic materials in which the stabilizer precursors of the present invention can be incorporated can contain one or more emulsions of any composition known in the art, e.g. chlorobromide or chlorobromoiodide emulsions, as well as bromide or bromoiodide emulsions which are preferred for graphics art camera materials because of their intrinsic higher sensitivity. In the case of reprographic duplicating materials, especially those of the daylight type, the emulsions usually contain a high amount of chloride, preferably at least 80%, and can be doped with a Group VIII metal, e.g. Rhodium or Iridium. Especially in the latter kind of photographic materials the incorporation of the compounds of the invention is very useful as was explained above. The emulsions can be of the conventional negative working type giving rise to a surface latent image. They can contain a spectral sensitizer but this will preferably not be the case in the particularly useful application in daylight stable graphic arts duplicating materials. They can be chemically sensitized but again, in the latter application that will preferably not be the case. Alternatively they can be of the direct positive type, e.g. externally prefogged and containing an electron acceptor, or of the unfogged type containing internal electron traps and working with nucleating agents and fogging development.

The photographic materials comprising the compounds of the invention can be composed of one single emulsion layer, as is the case for many applications, or they can be built up by two or even more emulsion layers. Beside the light sensitive emulsion layer(s) the photographic material can contain several non-light sensitive layers, e.g. a protective layer, one or more backing layers, one or more subbing layers, and one or more intermediate layers, e.g, filter layers.

Common additives well known in the photographic art can be present in the coated emulsion layer or in any other hydrophylic layer. So the material can contain a limited amount of the unmasked forms of the compounds of the invention or it can contain other conventional anti-foggants or stabilizers such as tetrazaindenes and pentazaindenes, especially those described by Birr in Z. Wiss. Phot. 47 (1952), pages 2-58.

The binder of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde. N-methylol compounds e.g. dimethylolurea and methyloldimethylhydantoin, dioxan derivatives e.g. 2,3-dihydroxy-dioxan active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic element of the present invention may further comprise various kinds of surface-active agents in the photographic emulsion layer or in at least one other hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Such surface-active agents can be used for various purposes e.g. as coating aids, as compounds preventing electric charges, as compounds improving slidability, as compounds facilitating dispersive emulsification, as compounds preventing or reducing adhesion. Preferred surface-active agents are compounds containing perfluorinated alkyl groups.

The photographic element of the present invention may further comprise various other additives such as e.g. compounds improving the dimensional stability of the photographic element, antistatic agents, spacing agents, light absorbing dyes, e.g. antihalation dyes, filter dyes or acutance dyes, lubricants, opacifying compounds, e.g. titanium dioxide, and plasticizers.

Antistatic agents can be used in one or more of the layers on the emulsion side or in a backing layer.

Suitable additives for improving the dimensional stability of the photographic element are e.g. dispersions of a water-insoluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids. Alpha-Beta-unsaturated dicarboxylic acids, hydroxyalkyl (meth)acrylates, sulphoalkyl (meth)acrylates, and styrene sulphonic acids.

Spacing agents can be present of which, in general, the average particle size is comprised between 0.2 and 10 micron. Suitable spacing agents can be made e.g. of polymethyl methacrylate, of copolymers of acrylic acid and methyl methacrylate, and of hydroxypropylmethyl cellulose hexahydrophthalate. Other suitable spacing agents have been described in U.S. Pat. No. 4,614,708. Spacing agents can also serve as matting agents. Other common matting agents consist of silica particles of which different size classes can be used.

The support of the photographic material may be opaque or transparent, e.g. a paper support or resin support. When a paper support is used preference is given to one coated at one or both sides with an Alpha-olefin polymer, e.g. a polyethylene layer which optionally contains an anti-halation dye or pigment. It is also possible to use an organic resin support e.g. cellulose nitrate film, cellulose acetate film, polyvinyl acetal film, polystyrene film, polyethylene terephthalate film, polycarbonate film, polyvinylchloride film or poly-Alpha-olefin films such as polyethylene or polypropylene film. The thickness of such organic resin film is preferably comprised between 0.07 and 0,35 mm. These organic resin supports are preferably coated with a subbing layer which can contain water insoluble particles such as silica or titanium dioxide.

The photographic materials of the present invention can be exposed in any convenient way according to their particular application, e.g. by daylight or by artificial light like tungsten light, xenon, metal-halogen lamps, quartz-halogen lamps, by laser sources or invisible radiation like ultraviolet, X-rays and infrared.

The processing of the photographic materials of the present invention proceeds according to specifications dependent on the particular use of the material.

Conventional "Rapid Access" developers are formulated by a combination of a developing agent, a superadditive developing agent and a high sulphite content. This leads to their practical advantage of wide processing latitude (development time and/or temperature) and excellent chemical stability of the developer solutions. These merits however are at the expense of superior dot and line quality.

Classical "lith" developers are characterized by a low free sulphite content and the application of hydroquinone as sole developing agent. This leads to infectious development systems which produce sharp edged pictures on halftone and line copies. Their chemical stability is very poor and need constant monitoring.

The new, so-called "hard dot Rapid Access" systems combine a high sulphite content with a mechanism in which a chemical species is sufficiently active to initiate an infectious development-like high contrast development. Possible mechanisms can be based on, but are not restricted to hydrazine, hydroquinone or tetrazolium salt chemistries. These systems have the superior quality of classical lith, systems in addition to the good chemical stability of the Rapid Access systems.

Usually the processing proceeds in an automatically driven apparatus, e.g. a RAPILIN, marketed by AGFA-GEVAERT N.V., provided with an automatic replenishment system.

The following examples illustrate the present invention without limiting it thereto.

EXAMPLE 1

1.a. Preparation of 1-(2-sulphonatobenzoyl)-5-nitroindazole trimethylamine salt (Compound I-1)

To a suspension of 179.5 g (1.1 mole) of 5-nitroindazole and 184 g (1 mole) of o-sulphobenzoic acid anhydride in 2000 ml of dry acetone were added dropwise whilst stirring 153 ml (1.1 mole) of triethylamine at reflux temperature. Then the suspension was refluxed for another 6 hours. The precipitate was filtered off at room temperature, washed with acetone and dried. Yield: 323 g (72%); melting point: 210° C.; chemical structure confirmed by NMR analysis.

1.b. Preparation of 1-(2-sulphonatobenzoyl)-5-nitroindazole potassium salt (Compound I-2)

To a suspension of 268.8 9 (0.6 mole) of 1-(2-sulphonatobenzoyl)-5-nitroindazole trimethylamine salt in 540 ml of methanol and 360 ml of water was added at room temperaure whilst stirring a saturated potassium chloride solution containing 134 g (1.8 mole) of potassium chloride in 400 ml of water. Then the suspension was stirred for another two hours. After waiting for 12 hours the precipitate was filtered off, washed with 480 ml of a water/methanol (1/1) mixture and finally dried. Yield: 217 g (94 %): melting point>300° C.

1.c. Preparation of 1-(2-sulphonatobenzoyl)-benzotriazole triethylamine salt (Compound I-3)

This compound was prepared in a similar way as explained in example 1.a, with the exception that 1.1 mole of benzotriazole was used instead of 5-nitroindazole. Yield: 56%: melting point 180° C.

1.d. Preparation of 1-(2-sulphonatobenzoyl)-5-methyl-benzotriazole triethylamine salt (Compounds (I-4)a and (I-4)b))

This compound was prepared in a similar way as explained in example 1.a. with the exception that 1.1 mole of 5-methyl-benzotriazole was used instead of 5-nitroindazole. A mixture of the two positional isomers (I-4)a and (I-4)b was obtained. Yield: 46%; melting point: about 167° C.

EXAMPLE 2

A cubic grain type silver iodobromide emulsion (1 mole % of iodide) having an average grain size of 0.3 micron, chemically sensitized with ammonium gold(III) thiocyanate and sodium thiosulphate, and stabilized with 4-hydroxy-6-methyl-1,3,3a,7-tetraazaindene was coated onto a subbed polyethylene terephtalate support at a gelatin coverage of 2.7 g/m$^2$ and a coverage of silver halide equivalent to 3.2 g of Ag/m$^2$. The emulsion layer further contained polyethylacrylate latex and 5-nitroindazole in amounts corresponding to 0.8 g/m$^2$ and 5 mg/m$^2$ respectively.

The silver halide emulsion layer was covered with a protective layer containing 0.6 g/m$^2$ of gelatin hardened with 1-(4-morfolinocarbamoyl)-4-(2-sulfoethyl)-pyridinium hydroxide inner salt. Separate areas of the photographic material were exposed in a vertical process camera REPROMASTER RPS 2001 (trade name), marketed by AGFA-GEVART N.V., through respectively a continuous tone wedge having a constant of 0.15 and a grey negative screen having a screen ruling of 54 lines per cm.

The development proceeded by dipping the exposed photographic materials into a tray for 40 s at a temperature of 38° C. using a Rapid Access developer having the following basic composition (part A):

| | |
|---|---|
| ethylenediamine-tetra-acetic-acid sodium salt | 1 g |
| sodium carbonate | 40 g |
| sodium bromide | 4 g |
| sodium sulphite anh. | 70 g |
| hydroquinone | 40 g |
| polyoxyethylene glycol | 200 mg |
| (average number of oxyethylene units being 70) | |
| water to make | 1 l |
| pH adjusted to 11.5 with sodium hydroxyde | |

To said basic composition were added 0.46 mmole/l of water soluble 5-nitroindazole precursors according to the invention as specified in table 1 below. In a comparison developer 0.46 mmole of 5-nitroindazole (5-NI) was added per liter. However this compound is only slightly soluble in this solution. Therefore a second comparison developer sample was included in which 5-nitroindazole was first dissolved in 30 ml of N-methyl-pyrrolidone (part B) and then added to the solution, replacing 30 ml of water. In each sample the pH was readjusted to 11.5 with sodium hydroxide.

The fixing proceeded in a tray at 25° C. for 3 min using a fixing bath with following composition:

| | |
|---|---|
| ammonium thiosulphate anhydrous | 100 g |
| sodium sulphite anh. | 10 g |
| boric acid | 5 g |
| sodium acetate | 15 g |
| acetic acid, glacial | 8 ml |
| water to make | 1 l |

In table 1 below the photographic speed is expressed in relative arithmetic values (rel. S) measured at density 3.00 above fog. The speed obtained with the comparison developer sample 1 was arbitrarely given the value 100. Gradient values in the toe of the sensitometric curve ($g_v$) were measured between the log exposure values at densities 0.1 and 0.6 above fog. Straight line gradient values (g) were measured between the log exposure values at densities 0.3 and 3.0 above fog.

The screen dot quality was assessed and the rating expressed by arbitrary numbers ranging from 0 to 5 wherein increasing numbers stand for degrading quality. Number 0 stands for developed screen dots having high optical density and sharp non-indented edges. The following numbers relate to screen dots having gradually reduced optical densities and dot edges with increasing indentation and fuzzy structure. At a rating value above 3 the quality is considered to be no longer commercially acceptable.

TABLE 1

| sample no. | devel. comp. | sensitometry | | | | dot rating |
|---|---|---|---|---|---|---|
| | | fog | rel. S | $g_v$ | g | |
| 1 comparison | + 5-NI | 0.03 | 100 | 4.3 | 12.8 | 2-3 |
| 2 comparison | + 5-NI/NMP | 0.03 | 97 | 8.3 | 21.0 | 1 |
| 3 invention | + comp. I-1 | 0.03 | 104 | 5.2 | 16.1 | 1-2 |
| 4 invention | + comp. I-5 | 0.03 | 112 | 5.7 | 16.0 | 1-2 |

It is apparent from the results presented in table 1 that excellent dot ratings and sensitometric results are obtained with the water soluble 5-nitroindazole precursors according to the present invention by which the use of organic solvents is made superfluous.

EXAMPLE 3

This example deals with the stability of gelatineous solutions containing masked or free 5-nitroindazole. A control composition (A) containing 100 g of inert gelatin in 1600 ml of water was prepared. The solution further contained matting agents and anti-halo dyes. In a second control composition (8) 300 ml of water was replaced by 300 ml of a 1% alcoholic solution of 5-nitroindazole. In a composition (C) 700 ml of water was replaced by 700 ml of a 1% aqueous solution of compound I-2 according to the invention; this amount is equivalent based on molecular weight to the amount of 5-nitroindazole present in (B). In each sample pH was adjusted to 6.5. The evolution of the viscosity (m.Pa.s) as a function of time was followed and denoted in table 2a; the appearance of crystallization, if any, was noted and represented in table 2b:

TABLE 2a

| | comp. | | |
|---|---|---|---|
| | A | B | C |
| viscosity after 1 h | 24 | 24 | 21 |
| " " 6 h | 26 | 25 | 22 |
| " " 24 h | 27 | 34 | 25 |

TABLE 2b

| crystall. after 1 h | no | no | no |
|---|---|---|---|
| " " 6 h | no | yes | no |
| " " 24 h | no | yes | no |

The results represented in table 2 illustrate the instability problems arising in compositions containing an alcoholic solution of 5-nitroindazole which can be overcome by replacing it by an aqueous solution of precursor compound I-2.

EXAMPLE 4

Gelatineous solutions according to the compositions A, B and C of the previous example were coated as backing layers (samples A', B', C') of a daylight stable graphic arts contact duplicating material. The gelatin coverage of the backing layers was 1 g/m$^2$ so that the backing layer of sample B' contained 30 mg/m$^2$ of 5-nitroindazol, the backing layer of invention sample C' contained 70 mg/m$^2$ of compound I-2 and the backing layer of control sample A' contained neither stabilizer nor stabilizer precursor. The emulsion layer which was the same for each sample contained a fine grained emulsion composed of 98% of chloride and 2% of bromide. It was coated at a coverage of 5.0 g Ag/m$^2$. This layer further contained conventional photographic additives. On top of it a protective layer was applied at a gelatin coverage of 1 g/m$^2$ of each material, 60 m$^2$, for 50% of the surface exposed by UV, were developed in a continuous way in a hard dot Rapid Access developer with the same basic composition as in example 2 and further containing initially 100 mg/l of 5-nitroindazole (5-NI) predissolved in N-methyl-pyrrolidone. After the passage through of these 60 m$^2$ the concentration of 5-nitroindazole was determined analytically and compared to the original value. The results are summarized in table 3.

TABLE 3

| | sample | | |
|---|---|---|---|
| | A' | B' | C' |
| mg/l 5-NI at start | 98 | 98 | 98 |
| " after 60 m$^2$ | 58 | 82 | 102 |

The results of table 3 clearly illustrate that the presence of invention compound I-2 in the backing layer of a photographic material assures the maintainance of a fairly constant level of the 5-nitroindazole concentration in the developer even in a better way than is the case with free 5-nitroindazole itself in the backing layer.

We claim:

1. Method for developing an imagewise exposed photographic material comprising a support and at least one silver halide emulsion layer characterized in that the developing step is carried out in the presence of a compound according to general formula (Ia) or (Ib):

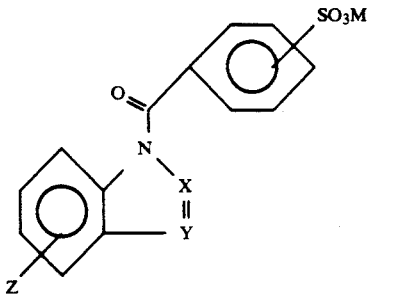

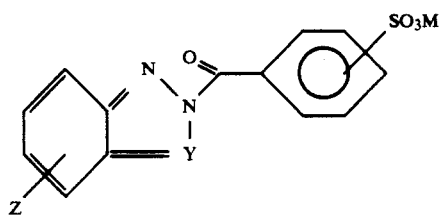

wherein
- X and Y each independently represent N or CR, R being hydrogen or lower alkyl,
- Z represents a lower alkyl group, a nitro group, a halogen atom or hydrogen, and
- M represents a positive counterion.

2. Method according to claim 1 wherein said compound according to general formula (Ia) or (Ib) is incorporated in a photographic developing solution.

3. Method according to claim 1 wherein said compound according to general formula (Ia) or (Ib) is incorporated in said photographic material.

4. Method according to claim 3 wherein said compound according to general formula (Ia) or (Ib) is incorporated in a silver halide emulsion layer of said photographic material.

5. Method according to claim 3 wherein said compound according to general formula (Ia) or (Ib) is incorporated in a layer coated at the side of the support opposite to that carrying the emulsion layer(s).

6. Photographic developing solution characterized in that it contains a compound according to several formula (Ia) or (Ib):

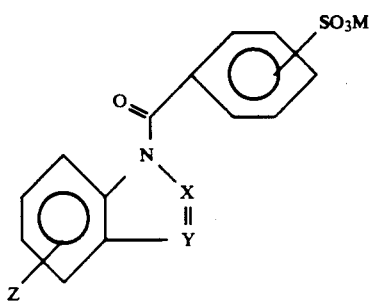

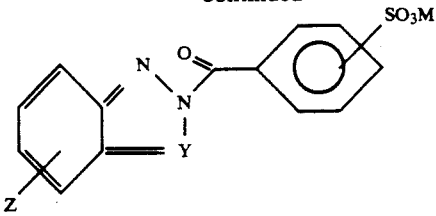

wherein
- X and Y each independently represent N or CR, R being hydrogen or lower alkyl,
- Z represents a lower alkyl group, a nitro group, a halogen atom or hydrogen, and
- M represents a positive counterion.

7. Photographic material comprising a support and at least one silver halide emulsion layer characterized in that it further contains a compound according to general formula (Ia) or (Ib):

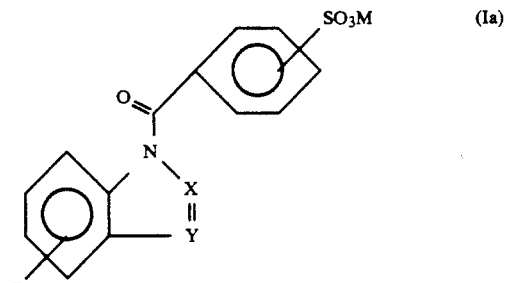

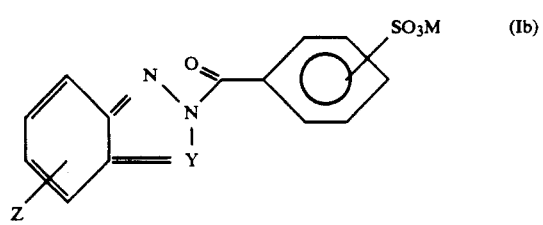

wherein
- X and Y each independently represent N or CR, R being hydrogen or lower alkyl,
- Z represents a lower alkyl group, a nitro group, a halogen atom or hydrogen, and
- M represents a positive counterion.

8. Photographic material according to claim 7 wherein the compound according to general formula (Ia) or (Ib) is incorporated in a silver halide emulsion layer.

9. Photographic material according to claim 7 wherein the compound according to general formula (Ia) or (Ib) is incorporated in a layer coated at the side of the support opposite to that carrying the emulsion layer.

10. Photographic material according to claim 7 wherein said material is a graphic arts hard dot Rapid Access material.

11. Photographic material according to claim 10 wherein said graphic arts hard dot Rapid Access material contains a silver halide emulsion the halide composition of which consists of at least 80% of chloride.

* * * * *